(12) United States Patent
Tarajano (10) Patent No.: US 10,653,227 B2
(45) Date of Patent: May 19, 2020

(54) HOLLOW UNPRESSURIZED BOUNCY COSMETIC APPLICATOR

(71) Applicant: L'Oréal, Paris (FR)

(72) Inventor: Lemis Tarajano, New York, NY (US)

(73) Assignee: L'Oréal, Paris (FR)

(*) Notice: Subject to any disclaimer, the term of this patent is extended or adjusted under 35 U.S.C. 154(b) by 47 days.

(21) Appl. No.: 15/828,046

(22) Filed: Nov. 30, 2017

(65) Prior Publication Data

US 2019/0159572 A1 May 30, 2019

(51) Int. Cl.
| A45D 33/00 | (2006.01) |
| A45D 34/04 | (2006.01) |
| A61M 35/00 | (2006.01) |
| A45D 40/28 | (2006.01) |
| B65D 83/00 | (2006.01) |

(52) U.S. Cl.
CPC ............ *A45D 34/04* (2013.01); *A45D 40/28* (2013.01); *A61M 35/003* (2013.01); *A45D 2200/051* (2013.01); *A45D 2200/1018* (2013.01); *A45D 2200/1036* (2013.01); *B65D 83/0055* (2013.01)

(58) Field of Classification Search
CPC ............ A45D 34/04; A45D 2200/1009; A45D 2200/1018; A45D 2200/1036
USPC ......................................................... 401/130
See application file for complete search history.

(56) References Cited

U.S. PATENT DOCUMENTS

| 1,439,734 A | 12/1922 | Guizburg |
| 2,002,144 A | 5/1935 | Heaton |
| 2,511,557 A | 6/1950 | Arnold |
| 2,621,784 A * | 12/1952 | Van Boytham ........ A45D 33/34 15/227 |
| 3,337,895 A | 8/1967 | Clements |
| 3,955,233 A | 5/1976 | Nakamura |
| 6,585,511 B2 * | 7/2003 | Dragan ............. B05C 17/00593 401/176 |
| 9,259,075 B2 * | 2/2016 | Gordon .................. A45D 34/04 |
| 9,307,827 B2 | 4/2016 | Brewer |
| 9,492,001 B2 * | 11/2016 | Luzon .................. A45D 34/041 |
| 9,750,533 B2 | 9/2017 | Brewer et al. |
| 10,117,811 B2 | 11/2018 | Aubert et al. |
| 2004/0031723 A1 | 2/2004 | Jean-Louis |
| 2004/0258457 A1 | 12/2004 | Legendre |
| 2017/0258203 A1 | 9/2017 | Crane et al. |

(Continued)

FOREIGN PATENT DOCUMENTS

| DE | 28 34 801 A1 | 2/1980 |
| WO | 2017/105045 A1 | 6/2017 |

OTHER PUBLICATIONS

International Search Report and Written Opinion dated Feb. 14, 2019, issued in corresponding International Application No. PCT/US2018/063128, filed Nov. 29, 2018, 14 pages.

(Continued)

*Primary Examiner* — Jennifer C Chiang
(74) *Attorney, Agent, or Firm* — Christensen O'Connor Johnson Kindness PLLC (57) ABSTRACT

A cosmetic applicator includes a first body having a hollow, unpressurized interior, wherein the first body is made at least in part from a material that is resilient. In one aspect, the cosmetic applicator further includes a cover removably securable on the first body. A coating for a cosmetic applicator includes a first body made at least in part from a material that is resilient and has a hollow, unpressurized interior.

12 Claims, 9 Drawing Sheets

(56) References Cited

U.S. PATENT DOCUMENTS

2018/0317628 A1* 11/2018 Villarreal ............... A45D 34/04
2018/0344007 A1* 12/2018 Huang .................. A45D 34/04

OTHER PUBLICATIONS

International Search Report and Written Opinion dated Dec. 12, 2018, issued in corresponding International Application No. PCT/US2018/048630, filed Aug. 29, 2018, 13 pages.

* cited by examiner

HOLLOW UNPRESSURIZED BOUNCY COSMETIC APPLICATOR

SUMMARY

A cosmetic applicator includes a first body having a hollow, unpressurized interior, wherein the first body is made at least in part from a material that is resilient. In one aspect, the cosmetic applicator further includes a cover removably securable on the first body.

At least a portion the first body has a predetermined rigidity, and at least one of the material of the first body and a wall thickness of the first body may at least partially determine the rigidity of the at least a portion of the first body.

The first body may include an opening providing access to the hollow, unpressurized interior.

A plug may be removably receivable within the opening.

The size of the opening may correspond to at least one of the material of the first body and a wall thickness of the first body for at least partially determining a rigidity of the at least a portion of the first body.

The configuration of the plug may correspond to at least one of the material of the first body and a wall thickness of the first body for at least partially determining a rigidity of the at least a portion of the first body.

The first body may be defined by a body having at least first and second sides and at least first, second, and third corners.

At least one of the first body and the coating may include at least one textured surface.

At least one of the first body and the coating may include at least a first area made from a first material and second area made from a second material.

A coating for a cosmetic applicator includes a first body made at least in part from a material that is resilient and has a hollow, unpressurized interior.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of this invention will become more readily appreciated by reference to the following detailed description, when taken in conjunction with the accompanying drawings, wherein.

DETAILED DESCRIPTION

Cosmetic formulations are often applied to a person's face, hair, skin, nails, etc. ("keratinous materials"), with an applicator, such as a brush, sponge, blender, bristle, cloth, etc. The configuration will depend on the intended end use. For instance, cosmetic formulas applied to (or removed from) the skin, such as the face, may be applied or removed with a sponge, cloth, blender, puff, etc. The sponge, cloth, blender, puff, etc., is not typically shaped to appropriately apply formulation to every contour of the face or another area of the body. For instance, a sponge may be an overall oval shape with flat sides. Although such a shape may be appropriate for applying a formulation to large areas of the face, the rounded edges may not be small enough to reach into more contoured areas of the face, such as under the eyes or nose.

A sponge, cloth, blender, puff, etc., may also have a density, firmness, etc., that is does not provide adequate sensorial effects during use. For instance, a denser, firmer sponge, a silicone blender, or the like may be too firm to provide a fingertip-like sensation to the user during application or removal of a cosmetic formulation. Such applicators are also often difficult to hold and/or manipulate against a keratinous material. As a result, a user may result to using his/her fingertips, which does not typically provide a desired cosmetic result (such as an airbrush look).

Many cosmetic applicators are difficult to clean and/or require frequent disposal and replacement. Moreover, most cosmetic applicators are also only suitable for a single use, such as foundation application, eye makeup application, make-up removal, etc. As a result, a user may be required to store multiple applicators for multiple uses and/or frequently replace the applicator.

Thus, an improved applicator that can be adapted for various uses (accurate application, removal, and/or cleansing of a cosmetic formulation), that provides improved sensorial effects, and that is easy to clean or otherwise hygienic to use is desired.

Referring to FIGS. 1-4, a first exemplary embodiment of a cosmetic applicator 20 will now be described in detail. The cosmetic applicator 20 is of a suitable shape, size, firmness, material, etc., for precisely and hygienically applying and/or removing a cosmetic formulation to/from a desired area of a user, such as the face, skin, nails, hair, etc. ("keratinous materials") while providing desired sensorial effects. In one embodiment, the cosmetic applicator 20 includes a hollow, unpressurized body 24 that is generally triangular in shape having first and second opposing convex sides 36 and 40, and first, second, and third corners 42, 44, and 46. The first and second sides 36 and 40 are sealed along their first and second lateral edges 50 and 52 to define an overall pillow shaped body 24 having soft edges. The body 24 includes a hollow, unpressurized interior 60 accessible through a bottom opening 66 defined by first and second opposing bottom edges 68 and 70. The first and second opposing bottom edges 68 and 70 may extend substantially straight across the bottom of the body 24 or they may be slightly concave to provide easier access to the hollow, unpressurized interior 60 of the body 24 and/or easier removal of any interior component received within the hollow unpressurized interior 60.

In that regard, the hollow, unpressurized interior 60 of the body 24 may be shaped and sized to receive at least one of a user's finger, a plug, a pressurized core, a cosmetic tool, or any other suitable interior component or other structure. For instance, in one embodiment, the hollow, unpressurized interior 60 of the body 24 is suitable shaped and sized to receive a user's finger during use. In such a cosmetic applicator configuration, the user may position the body 24 on the index finger or another finger, and then use the applicator to apply/remove cosmetic formulation similar to using a fingertip. However, by using the cosmetic applicator rather than a fingertip, enhanced application and/or cleansing effects can be achieved. The cosmetic applicator may be made from a preselected material, thickness, surface finish, etc., as will be described below, to provide the sensorial effects similar to using a fingertip.

In one embodiment, the body 24 may include internal structure such as webbing (not shown) that simply increases the rigidity of one or more portions of the body 24 and/or defines two or more interior hollow, unpressurized compartments. In the embodiment depicted in FIGS. 1-4, the body 24 is shown removably receiving a plug 74. The plug 74 is generally configured to be removably received within the bottom opening 66 of the body 24 to increase or decrease the rigidity of the body 24 or at least a portion thereof.

The plug 74 may be any suitable configuration for desirably adjusting the rigidity of the body 24 when received within the bottom opening 66. In the depicted embodiment, the plug 74 includes a cover portion 76 that is generally the same size and shape as the overall combined shape of the bottom opening 66 and the bottom edges 68 and 70, or slightly larger in size to define a circumferential lip for easily disengaging the plug 74 from the body 24. The cover portion 76 may also have an overall generally curved shape (with a concave exterior surface and a convex interior surface) to substantially match the curvature of the bottom edges 68 and 70. With such a curved configuration, a user may easily engage the exterior surface of the cover portion 76 with a finger or thumb for ergonomic gripping. In the alternative or in addition thereto, the exterior surface of the cover portion 76 may be used for applying/removing a cosmetic formulation.

The plug 74 further includes an insertion portion 78 extending from the interior surface of the cover portion 76 that is sized and shape to be received within the bottom opening 60 of the body 24 for removably retaining the plug 74 within the body 24. The insertion portion 78 may be any suitable configuration, such as generally annular in shape and substantially the same size and shape as the bottom opening 60 to define a friction fit between the insertion portion 78 and the body 24. Any other configuration may instead be used to removably secure the plug 74 within the bottom opening 60.

The plug 74 may also be any suitable material for adjusting the overall rigidity of the body 24 when received therein. For instance, the plug 74 may be made from a flexible and/or deformable material to add less rigidity to the body 24, or the plug 74 may be made from a firmer material, such as plastic, to add more rigidity to the body 24. The thickness and/or configuration of the plug 74 may also be adjusted to change the rigidity. For instance, a thicker plug 74 will add more rigidity to the body 24 while a thinner plug 74 will add less rigidity to the body 24.

As can be appreciated, with the bottom opening 66 left uncovered, the body 24, if made from a softer material, may easily flex, collapse, deform, bend, etc., resulting in less application control for the user. As a specific example, the first and second opposing sides 36 and 40 may easily collapse inwardly toward each other with no plug inserted into the bottom opening. Such a cosmetic applicator configuration may be difficult to use for cleansing, blending, etc. However, with a plug (such as plug 74) disposed in the bottom opening 60, the overall rigidity of the body 24 is increased and the body 24 would not easily collapse, providing additional application control for the user.

The triangular shape (i.e., two sides, three corners, and an optional bottom plug) of the cosmetic applicator 20 is optimized for applying/removing a cosmetic formulation to/from precise, targeted areas while at the same time being suitable for applying/removing a cosmetic formulation to/from a larger area. More specifically, the corners 42, 44, and 46, and edges 50 and 52 of the pillow-shaped body 24 and the areas of the opposing sides 36 and 40 near the corners and edges are suitable for applying/removing a cosmetic formulation to/from a more contoured or narrow area, such as around the eyes, nose, chin, etc. At the same time, the larger surface area of the first and second opposing sides 36 and 40 (and optionally the exterior surface of the plug 74) define a larger application area for application/removal of a cosmetic formulation to a larger surface area, such as the cheeks and forehead of the face.

In other embodiments, the body may include specially shaped portions for targeted application, such as cone-shaped areas, pointed areas, etc. Thus, it can be appreciated that the contoured shape of the body 24 can precisely fit within the edges, contours, hollows, etc., of a user's body with suitable sensorial effects to allow gentle and precise application or removal of a cosmetic formulation onto or from the skin, hair, scalp, nails, etc. A suitable handle, tab, etc. (not shown), solid or flexible, may extend from the body 24 for gripping and using the body 24 during application. The body 24 could also be configured to be attached to one or more different types of handles depending on the end use.

Although the exemplary embodiments of the cosmetic applicators are shown as triangle-shaped with first and second opposing sides, the cosmetic applicators may instead having hollow, unpressurized bodies of any suitable shape or geometry. For instance, in alternative embodiments, the cosmetic applicator may have a body that is square, oval, cylindrical, or cone-shaped, or any other suitable regular or irregular shape. The shape may be depend on the cosmetic formula being application (i.e., different shapes may be used for foundation, lip gloss, eye shadow, nail polish, cleansers, etc.) and/or the area on which it is being applied (i.e., face, nails, lips, eyes, etc.)

The body 24 is made from a suitably soft material such that it is at least somewhat flexible and resilient (i.e., it returns to its original shape). In this manner, the shape and contour of the body 24 can adapt to the contours of the user's skin, hair, nails, etc., during use for a superior blending or application effect. In some embodiments, the body 24 is suitable soft to substantially conform to a user's finger, a core, a plug, etc., inserted into or otherwise define within the hollow unpressurized interior 60. For instance, when the body 24 substantially conforms to the shape of a user's finger, the body 24 essentially defines a second skin application surface of the user for an enhanced sensorial effect. The soft and resilient nature of the body also makes it easier for the user to grasp and hold the applicator during use and/or position it over a finger for precise blending, cleansing, etc. At the same time, the material of the body 24 is also sufficiently rigid (e.g., has a minimum durometer or shore hardness value) to provide sufficient structure (with or without a plug or other insert) during use. For instance, the body 24 must be sufficiently rigid such that it does not simply collapse, bend, deform, etc., when being used for application or removal of a cosmetic application.

The hollow design of the body combined with a suitably soft and resilient yet somewhat rigid material causes the hollow body to provide a cushioning or bouncy sensation to the user during use. For instance, a cushioning or bouncy sensation may result during makeup application or blending through a dabbing or gliding motion. This cushioning or bouncy sensation enhances the sensorial experience for the user, which can benefit makeup application and blending, cleansing, etc.

Any suitable hygienic material may be used, like a non-porous, solid material such as silicone, a thermoplastic elastomer, a closed-cell foam, or the like. The chosen material may depend on the designated body shape, the size/shape of the hollow interior, the body wall thickness, the intended application, whether any plug, core, etc., is received or defined within the body, etc. For instance, an applicator having a greater wall thickness (such as between about 5-10 mm) may be made from a softer material. A similarly shaped applicator having a smaller wall thickness (such as between about 2-4 mm) may be made from a firmer material. Along the same lines, a thinner applicator body may be used with a plug, core, or internal webbing (not shown) to help increase the rigidity without adding thickness. As a non-limiting example, the cosmetic applicator 20 shown in FIGS. 1-3 may have a body 24 made from silicone having a wall thickness between about 1 mm and 10 mm.

The body 24 may also vary in wall thickness (such as between about 0.1 mm and 10 mm) to provide a more firm (with a thicker material) or less firm (with a thinner material) area(s) of the body. As a specific example, the wall may be thinner in the larger areas of the body 24 (such as the first and second opposing sides 36 and 40), and thicker in the smaller areas of the body, such as in the corners or more pointed areas. As yet another example, a first side of the body 24 may have a first wall thickness and an opposite side of the body 24 may have a second wall thickness.

The material of the body 24 may be either transparent, translucent, opaque, foiled or metallized, patterned, etc., in whole or part, and/or coated at least partially with a transparent, translucent, or opaque material or film. For instance, in some embodiments, the body 24 will be transparent such that when the hollow interior is occupied by a finger of a user, a plug, etc., it can be easily seen by the user. In other embodiments, the body 24 is a certain translucent or transparent material having a designated color for corresponding to an intended application. In other embodiments, certain portions of the body 24, such as the corners, are of a certain translucency and/or color to indicate a target area for application. The body 24 may also be made from and/or coated with a suitably waterproof material such that it may be easily cleaned and reused for various applications and such that cosmetic formulation transfer may be substantially prevented.

The material or outer surface of the body 24 may also vary in surface roughness/texture, shape, coefficient of friction, etc., in different areas of the body. A lower coefficient of friction on the outer surface of the body may provide a non-sticky surface for a smoother application of certain cosmetic formulations (such as lip gloss), wherein a textured surface may be more suitable for cleansing or application of other types of cosmetic formulations. The texture may be created by cutting or defining a pattern in the body material during a molding process, with flocking, coating, etc.

Figure 13:
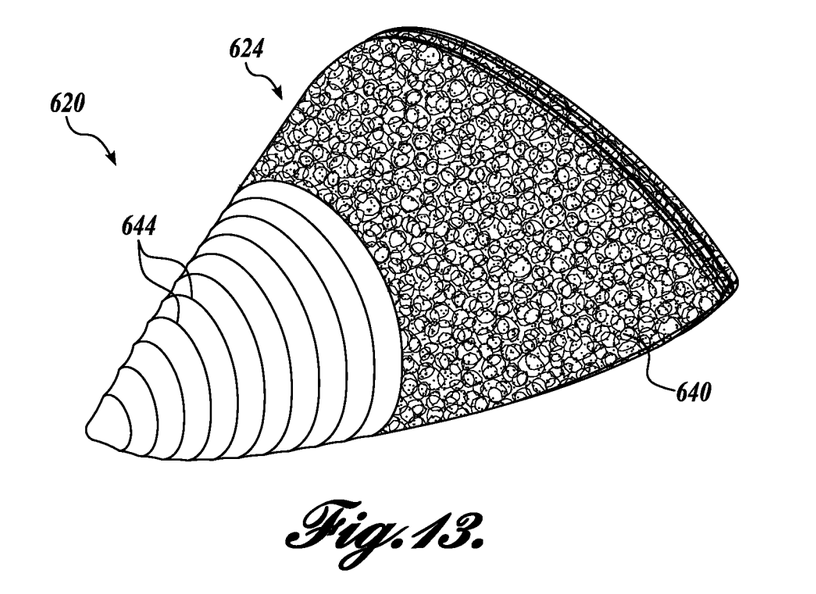
FIG. 13 is an isometric view of a cosmetic applicator formed in accordance with another alternative exemplary embodiment of the present disclosure.

For instance, in an alternative embodiment of a cosmetic applicator 620 shown in FIG. 13, the hollow, unpressurized body 624 includes a first outer surface area having flocked material 640, and a second outer surface area having ridges 644. The flocked area 640 may be used to substantially evenly apply powder or viscous foundations to a user's face or other skin, while the ridged area 644 may be used for cleansing or removal of a cosmetic formulation.

Figure 14:
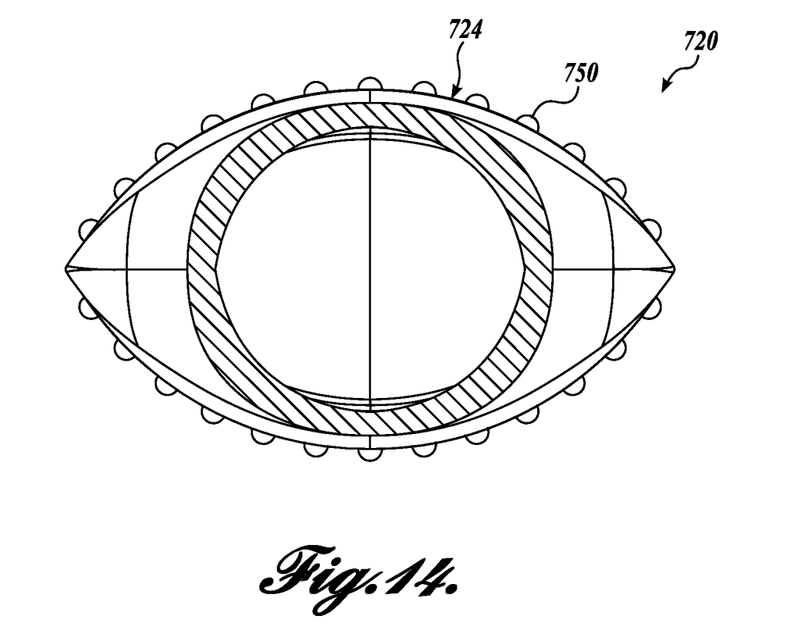
FIG. 14 is a cross-sectional view of a cosmetic applicator formed in accordance with another alternative exemplary embodiment of the present disclosure.

In another exemplary embodiment of a cosmetic applicator 720 shown in FIG. 14, the hollow, unpressurized body 724 includes bumps 750 on a bottom portion of the outer surface of the body. In other applications, the entire outer surface of the body 724 may include bumps or other texture. The bumps 750 may be used for increased gripping of the body during use, for cleansing, or for other uses. The cosmetic applicator may instead include any other suitable surface texture, shape, coefficient of friction, etc., in one or more areas of the body.

Figure 1:
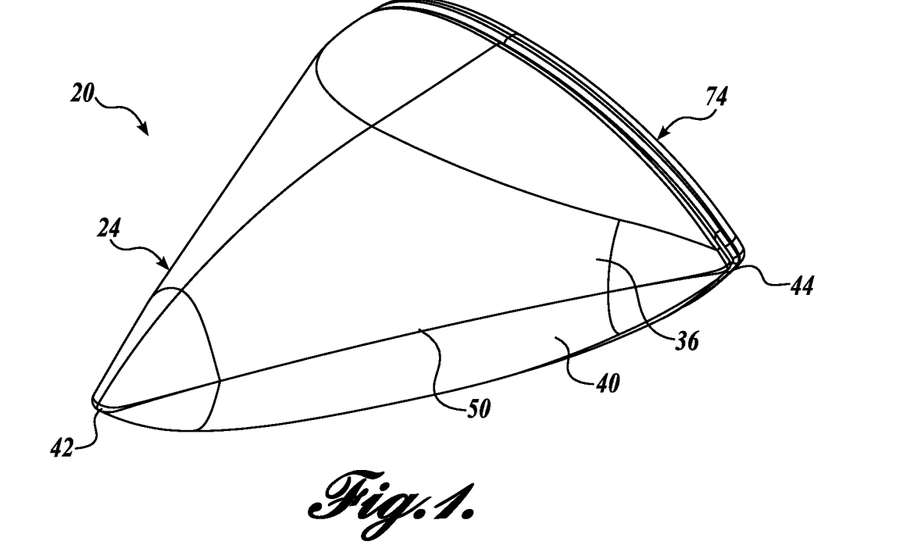
FIG. 1 is an isometric view of a cosmetic applicator formed in accordance with an exemplary embodiment of the present disclosure.
Figure 2:
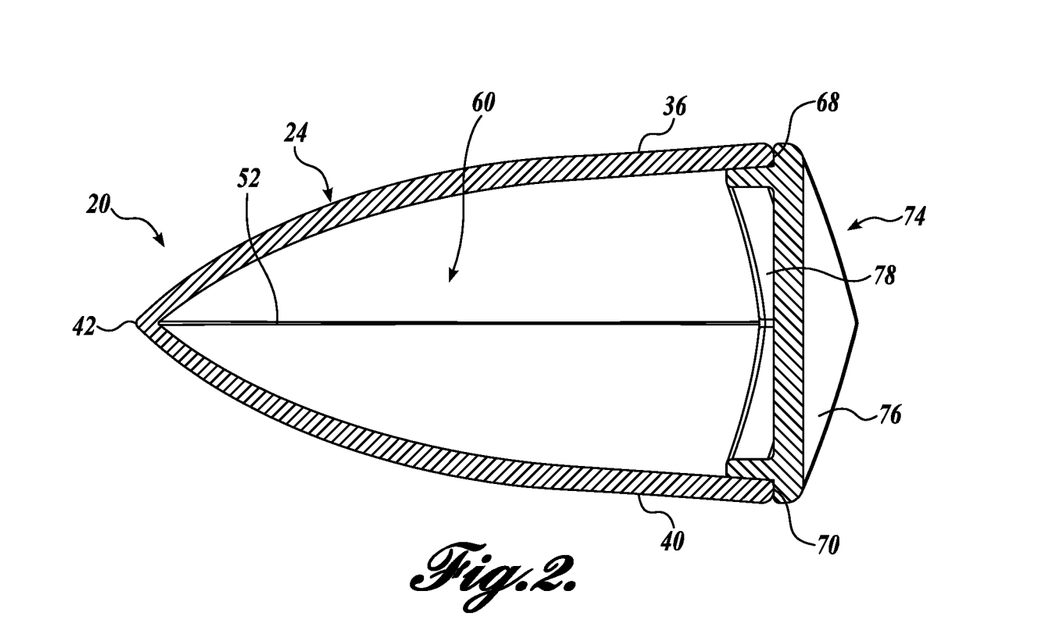
FIG. 2 is a cross-sectional view of the cosmetic applicator of FIG. 1.
Figure 3:
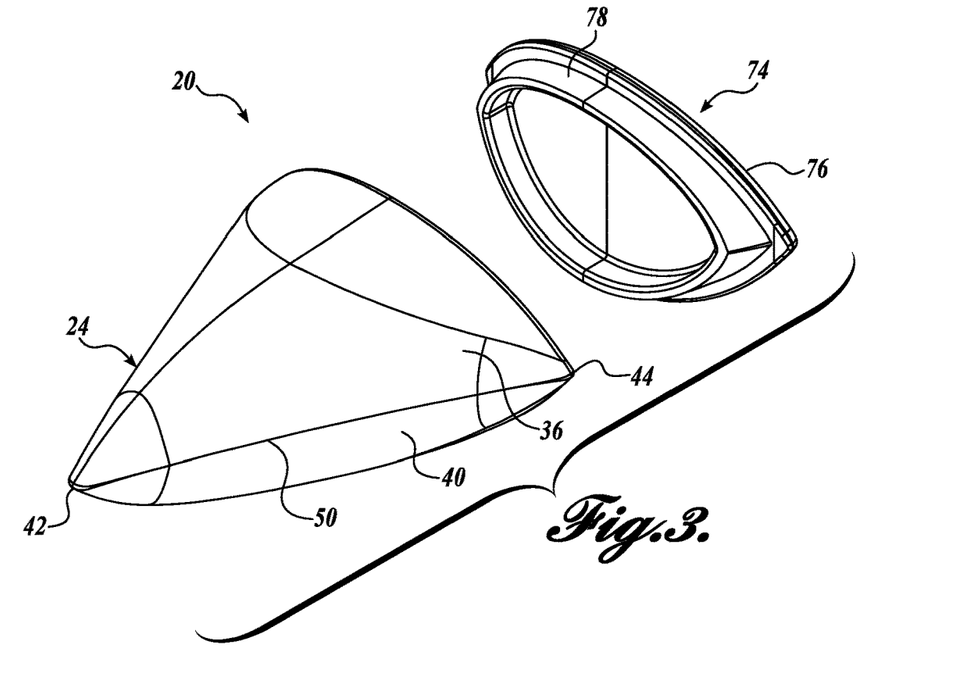
FIG. 3 is a first exploded view of the cosmetic applicator of FIG. 1.
Figure 4:
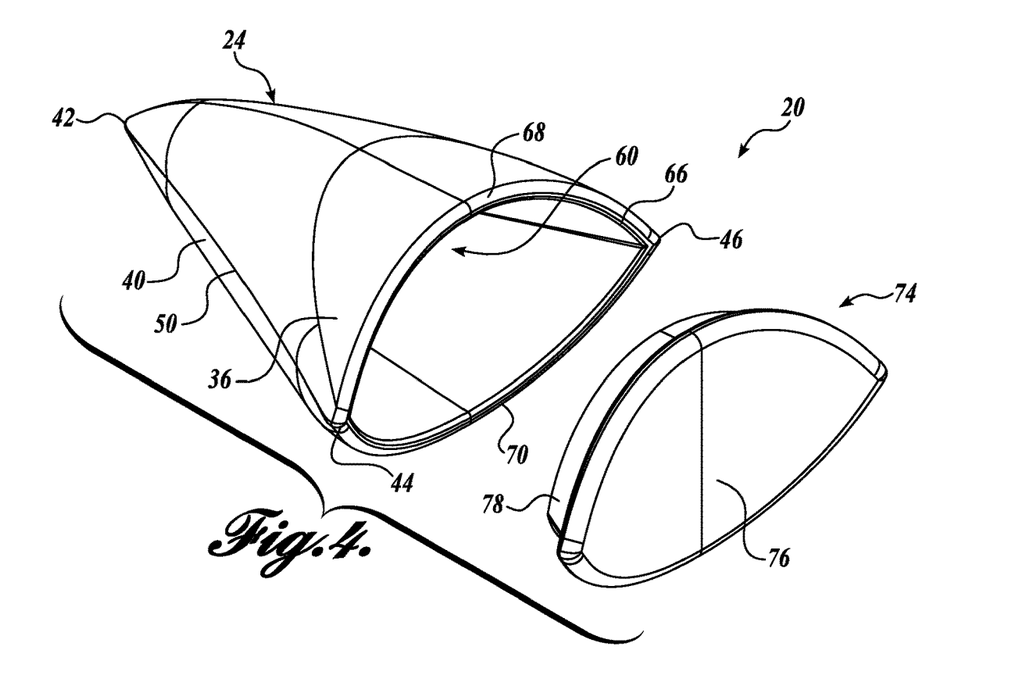
FIG. 4 is a second exploded view of the cosmetic applicator of FIG. 1.
Figure 5:
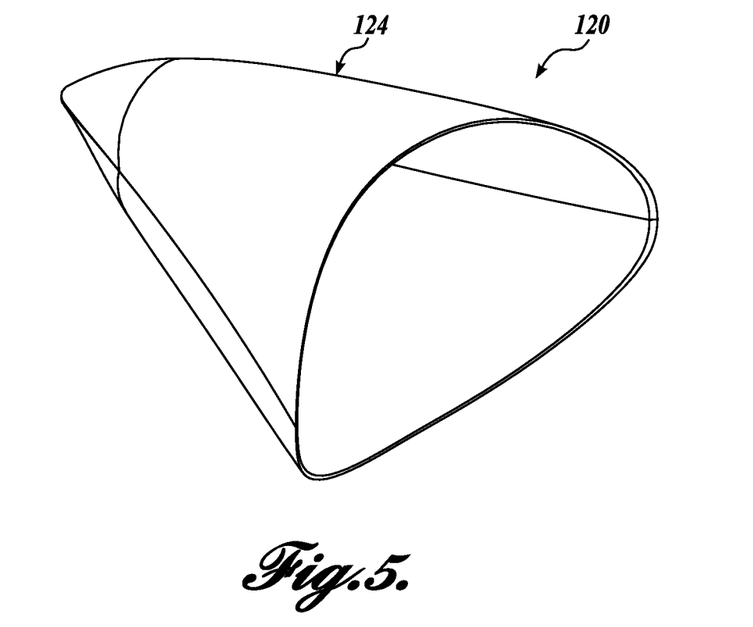
FIG. 5 is an isometric view of a cosmetic applicator formed in accordance with an alternative exemplary embodiment of the present disclosure.

Referring to FIG. 5, an alternative exemplary embodiment of a cosmetic applicator 120 is depicted. The cosmetic applicator 120 is substantially identical to the cosmetic applicator 20 described above except that the hollow, unpressurized body 124 is substantially thinner. A thinner body may be useful in applications where less rigidity is desired, where a more rigid material is used to define the body, where a plug, core, insert, internal webbing, etc., is disposed within the hollow interior of the body to increase rigidity, or in other applications.

Figure 6:
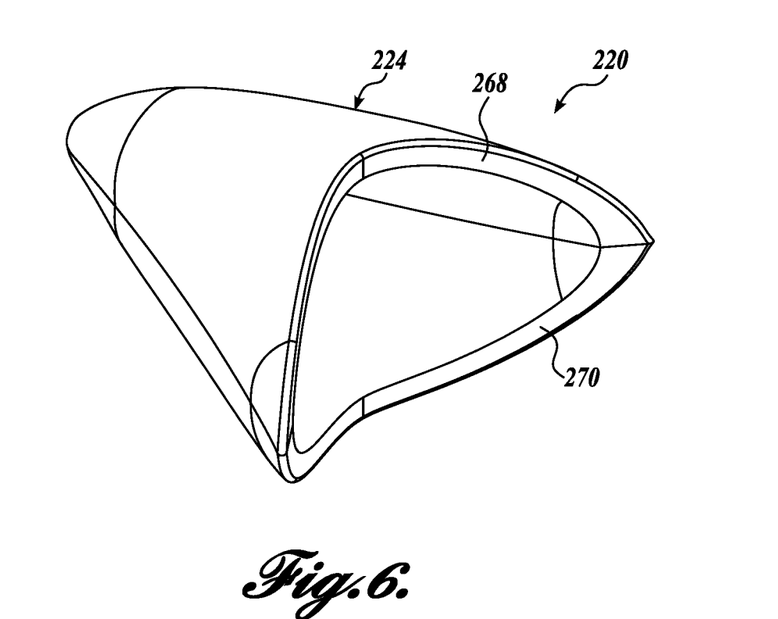
FIG. 6 is an isometric view of a cosmetic applicator formed in accordance with another alternative exemplary embodiment of the present disclosure.

Referring to FIG. 6, another alternative exemplary embodiment of a cosmetic applicator 220 is depicted. The cosmetic applicator 220 is substantially similar to the cosmetic applicator 20 described above except that the hollow, unpressurized body 224 has a substantially thicker wall. A thicker body wall may be useful in applications where more rigidity is desired, where a less rigid material is used to define the body, where a plug, core, insert, internal webbing, etc., is not disposed within the hollow interior of the body, or in other applications. The body 224 is also slightly different in shape than the body 24 described above in that the first and second bottom edges 268 and 270 define more of soft concave V-shape rather than extending substantially straight or gently curving across the bottom of the body. The concave V-shape of the bottom edges may increase grippability and/or usability of the body 224 for certain applications.

Figure 7:
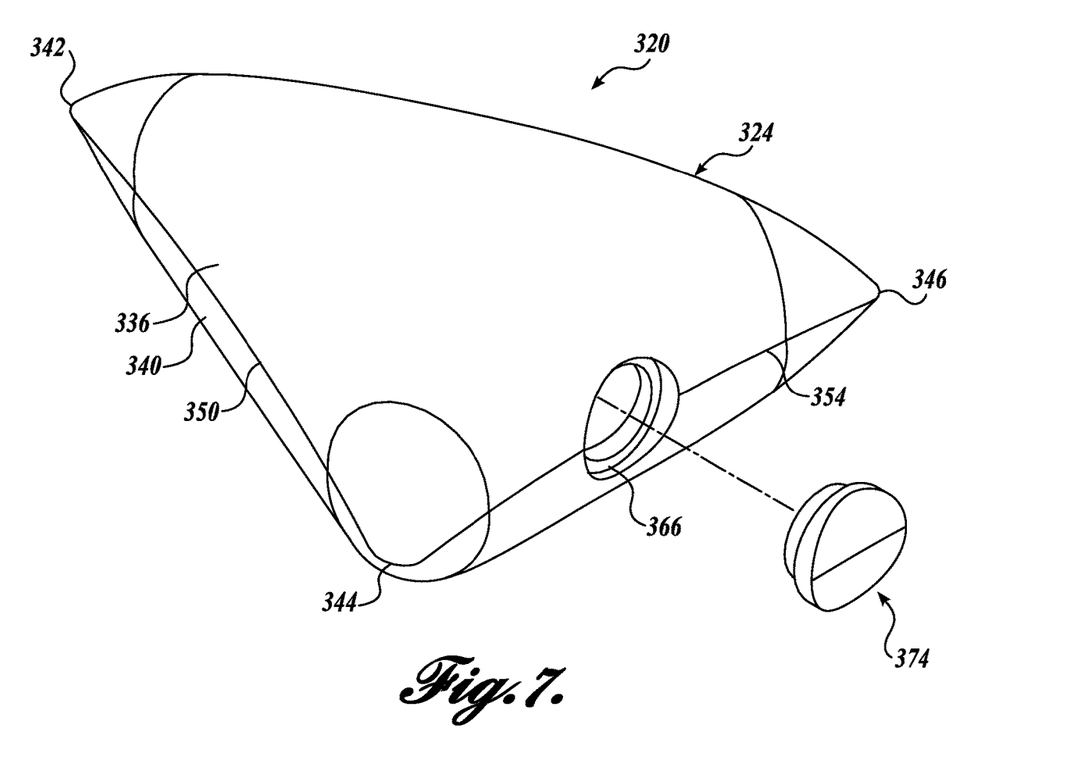
FIG. 7 is an isometric view of a cosmetic applicator formed in accordance with another alternative exemplary embodiment of the present disclosure.

Referring to FIG. 7, another alternative exemplary embodiment of a cosmetic applicator 320 is depicted. The hollow, unpressurized body 324 of the cosmetic applicator 320 is substantially similar to the body 24 of the cosmetic applicator 20 described above in that it includes first and second opposing convex sides 336 and 340, and first, second, and third corners 342, 344, and 346, wherein the first and second sides 336 and 340 are sealed along their first and second lateral edges 350 and 352. The body 324, however, is also sealed along a bottom edge 354 extending between the bottom corners 344 and 346 to define an overall substantially enclosed pillow shaped triangular body 324 having soft edges. In that regard, the body 324 includes a smaller bottom opening 366 (compared to bottom opening 66) defined along the bottom edge 354 and extending partially onto the first and second opposing sides 336 and 340. The bottom opening 366 is configured to removably receive a correspondingly-shaped plug 374 that is substantially similar to the plug 74 described above except scaled down in size to fit the bottom opening 366.

Compared to the body 24, the body 324 is also somewhat thicker. Accordingly, with a thicker body wall and mostly enclosed bottom portion, the body 324 (without a plug or with a plug, respectively) is more rigid than the body 24 (without a plug or with a plug, respectively). Inserting or removing a plug or other internal structure, such as webbing, can be used to increase or decrease the rigidity of either body 24 or 324. It can also be appreciated a hollow body having a smaller bottom opening, such as body 324, is more rigid overall without even increasing the wall thickness. Accordingly, it can be appreciated that many different design factors can be varied, such as shape, bottom opening size, the use of a plug or other internal structure, wall thickness, material, etc., to adjust the rigidity of one or more portions of the body.

Figure 8:
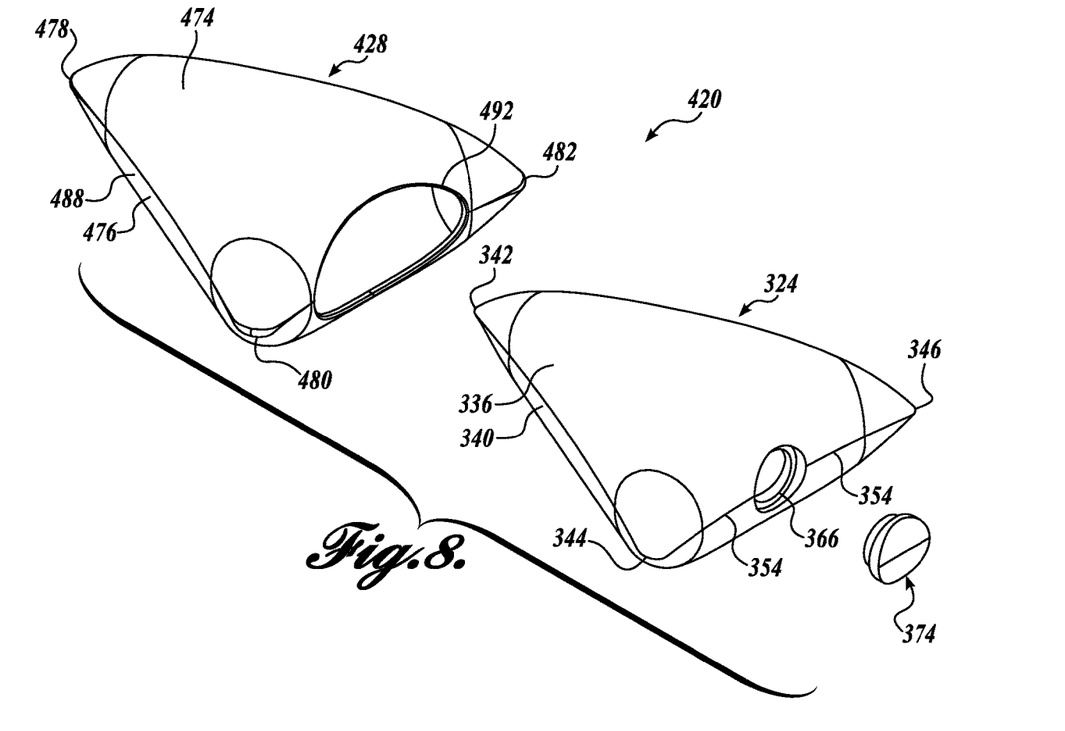
FIG. 8 is an isometric view of a cosmetic applicator formed in accordance with another alternative exemplary embodiment of the present disclosure.
Figure 9:
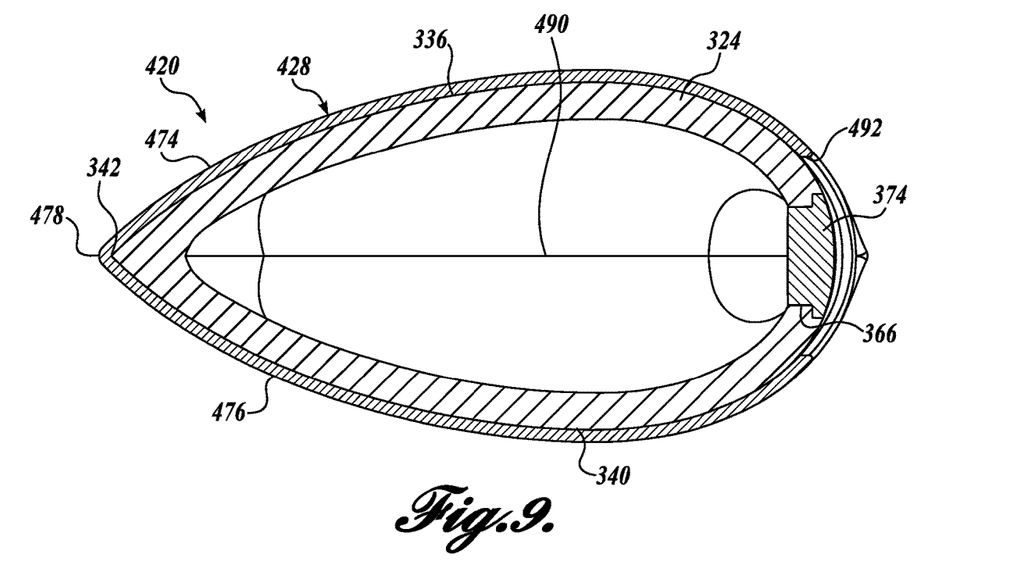
FIG. 9 is a cross-sectional view of the cosmetic applicator of FIG. 8.

Referring to FIGS. 8-9, another alternative exemplary embodiment of a cosmetic applicator 420 is depicted where a hollow, unpressurized body, such as body 324, is optionally enveloped or enclosed by a removable, washable, and/or disposable cover 428. The cover 428 may be used for application or removal of certain cosmetic formulations that cannot otherwise be applied or removed with the hollow body 324 or any other suitable hollow body, and/or to provide a different sensorial experience during application than would happen with the body alone. It should be appreciated that the body 324 may be used with or without the cover 428, and the cover 428 may be configured for use with any suitable hollow body.

In the depicted embodiment, the cover 428 is configured to envelope or enclose the body 324 in a manner such that the cover 428 substantially and tightly conforms to the shape of the body 324 to precisely fit (together with the body 324) within the edges, contours, hollows, etc., of a user's body with suitable relief to allow gentle and precise application or removal of a cosmetic formulation. In that regard, the cover 428 is substantially triangle shaped, having first and second opposing sides 474 and 476, and first, second, and third corners 478, 480, and 482. The first and second sides 474 and 476 are sealed along first and second lateral edges 488 and 490 to define an overall pillow shaped cosmetic applicator 420 (when received on the body 324) having soft edges. With the cover 428 substantially conforming to the shape of the body 324, the cosmetic applicator 420 will allow the user to adjust the expected make-up result and the coverage level.

In addition to or in lieu of a tightly conforming fit, the interior surface of the cover 428 may be temporarily or permanently glued to or otherwise attached to the outer surface of the body 324 to minimize any shifting, bunching, or movement of the cover 428 relative to the body 324 during use. In that regard, the outer surface of the body 324 and/or the interior surface of the cover 428 may include one or more adhesive portions that are initially covered by a releasable backing that may be removed prior to use. In an alternative embodiment, the outer surface of the body 324 and/or the interior surface of the cover 428 may be coated with a tacky or other high-friction material to minimize movement of the cover 428 relative to the body 324.

The cover 428 further includes an opening through which the body 324 may be inserted for disposing the cover 428 on the body 324 (and through which any handle, tab, etc., extending from the body 324 may protrude and/or through which a plug or other interior structure may be accessible). Any suitable opening may be used, such as an elastic opening 492 defined along a bottom portion that may be stretched over the body 324. In the alternative, the opening may be defined by a non-elastic opening that is enclosable by a hook and loop fastener (Velcro®), a zipper, or another suitable enclosure mechanism. The opening 492 allows the cover 428 to be removable from the body 324 and replaceable with a clean or different cover. In this manner, various different covers may be used with a single body. In other words, the cover may be changed depending on the intended application or desired sensorial effect. For instance, the customizable cover will allow for the applicator to be used for skin and/or hair cosmetic formulation application and/or removal.

In that regard, the cover 428 may be made from any suitable material having a suitable porosity, density, durometer, firmness, thickness, etc., for the desired application and aesthetic effect. For instance, the cover 428 may be between about 1 mm to 6 mm thick. Moreover, the cover 428 may vary in thickness in different areas of the cover. For instance, the corners may be thicker than the sides or edges of the cover 428.

With regard to material, in some exemplary embodiments, the cover 428 may be made from a sponge material, a foam (an open or closed cell foam, a flocked foam, etc.), a suitable fabric (e.g., fiber or microfiber material), etc., that is configured for depositing or removing a cosmetic formulation to a user's face, skin, hair, etc. For make-up application, the cover 428 may be configured to deposit a continuous film of a pigmentary solution (powder or liquid) onto the skin to obtain a substantially even coverage. An open cell foam material (PU, PE, etc.) may be used when some absorption of the cosmetic formulation on the cover 428 is desired for an even application, for thicker foundations, etc. A closed cell foam material (such as NBR) may be used to prevent absorption of the cosmetic formulations by the cover 428 and to substantially keep the body 324 from getting dirty or covered with cosmetic formulation. If a flocked material is used, a flocked material having a longer length may be used for applying a low viscous material, wherein a flocked material having a shorter length may be used for applying a high viscous material.

One or more surfaces or areas of the cover 428 (and optionally the body 324) may also include patterned areas, grooves, surface bumps, protrusions, textures, areas of changing color, etc., to aid in the application or removal of a cosmetic formulation, to indicate an intended area of use for a specific application, and/or to provide an aesthetically pleasing cover. In some embodiments, the cover 428 may be made from cotton or another soft or absorbent material that aids in removing dirt, makeup, or other debris from the skin or other surface. For make-up removal, the cover 428 may be used with the appropriate make-up remover formula to allow for a gentle removal of the cosmetic formulation previously applied (liquid or powder types). In such a configuration, the cosmetic formulation is removed gently, without clogging any pores, leaving the skin and the face very clean without substantial irritation.

In other embodiments, the cover 428 and/or the body 324 may be laminated with a suitable foam or other material. For instance, the cover 428 and/or the body 324 may be laminated with a composite material known by the name of PolyDry™, available from Creative Foam Medical Systems of Bremen, Ind. As a specific example, the composite material may be applied by thermopressure welding.

In one embodiment, at least a portion of an outer surface of the cover 428 and/or the body 324 is flocked using nylon (PA) fibers or any other suitable material.

The cover 428 (and optionally the body 324) may also be made from or treated with a suitable material that increases wetting of an aqueous phase of any cosmetic formulation on the surface of the cover 428 (and optionally the body 324). In one embodiment, one or more portions of the cover 428 (and optionally the body 324) may be comprised of at least one hydrophilic or a superhydrophilic material.

The wettability of a region can be determined using various technologies and methodologies including contact angle methods, the Goniometer method, the Whilemy method, or the Sessile drop technique. Wetting is a process by which a liquid interacts with a solid. Wettability (the degree of wetting) is determined by a force balance between adhesive and cohesive force and is often characterized by a contact angle. The contact angle is the angle made by the intersection of the liquid/solid interface and the liquid/air interface. Alternatively, it is the angle between a solid sample's surface and the tangent of a droplet's ovate shape at the edge of the droplet. Contact angle measurements provide a measure of interfacial energies and conveys direct information regarding how hydrophilic or hydrophobic a surface is. For example, superhydrophilic surfaces have contact angles less than about 5°, hydrophilic surfaces have contact angles less than about 90°, hydrophobic surfaces have contact angles greater than about 90°, and superhydrophobic surfaces have contact angles greater than about 150°. (see, e.g., U.S. Publication No. 2013/0131575, entitled "Systems, Devices, and Methods Including Infection-Fighting and Monitoring Shunts," the disclosure of which is hereby incorporated by reference herein in its entirety).

As a specific example, the cover 428 (and optionally the body 324) may be treated with one or more hydrophilic coatings, including polyvinylpyrolidone (PVP), polyurethanes, polyacrylic acid (PAA), polyethylene oxide (PEO), and/or polysaccharides. In the alternative or in addition thereto, the cover 428 (and optionally the body 324) may be treated to increase the surface energy of the cover 428 (and optionally the body 324), such as with a plasma treatment.

In another example, the cover 428 (and optionally the body 324) may be comprised of or otherwise treated with one or more hydrophobic or superhydrophobic coatings such as manganese oxide polystyrene ($MnO_2$/PS) nano-composite, zinc oxide polystyrene (ZnO/PS) nano-composite, precipitated calcium carbonate[3], carbon nano-tube structures, and/or silica nano-coating.

Additional non-limiting examples of materials that affect wettability of a surface include, but are not limited to, amphoteric surfactants, anionic surfactants, cationic surfactants, non-ionic surfactants, and the like.

In the alternative or in addition thereto, the cover 428 (and optionally the body 324) may comprise one or more nanostructures, microstructures, hierarchical structures, and the like that affect wettability of a surface. Non-limiting examples of nanostructures, microstructures, hierarchical structures, and the like include nanopatterned, micropatterned, and the like polymeric coatings. Specific examples include patterned silicon surface, perfluorodecyltriethyoxysilane (PFDTES) coatings, poly (methyl methacrylate) (PMMA) patterned structures, polystyrene (PS) (hydrophobic) patterned structures, and the like.

The above-noted treatments may be applied to any suitable portion of the cover 428 (and optionally the body 324). The cover 428 (and optionally the body 324) may also have one or more portions made from and/or coated with a first type of material and one or more portions made from and/or coated with a second type of material. For instance, the first side 474 of the cover 428 may have a first material/coating and the second side 476 of the cover 428 may have a second material/coating. In addition or in the alternative thereto, the first, second, and third corners 478, 480, and 482 of the cover 428 may be covered with a different material/coating for precise application/removal of a cosmetic application to/from a target area. In one embodiment, the interior of the sides and the corners of the cover 428 can be waterproof treated to substantially avoid any transfer of the cosmetic formulation onto the body 324.

It should also be appreciated that the surface properties of the cover 428 (and optionally the body 324) may be defined in any suitable manner. For instance, the cover 428 (and optionally the body 324) itself may be made from a hydrophilic material or hydrophobic material. In the alternative, the cover 428 (and optionally the body 324) may be made from any suitable material, and one or more surfaces of the cover 428 (and optionally the body 324) may be treated with a hydrophilic material or hydrophobic material. Moreover, the cover 428 (and optionally the body 324) may be treated, coated, sprayed, etc., with a suitable material in any suitable manner. In addition, the cover 428 (and optionally the body 324) may be textured or patterned with a coating in a suitable manner.

The cover 428 may have a suitable amount of elastic such that the cover 428 may be stretched over and secured on the body 324 after the body 324 is passed through the opening 492. In the alternative, the cover 428 may be made from a non-elastic material, with the body 324 being passed through the opening 492 in the cover 428 after the body 324 is deformed and/or any interior core, plug, etc., it is at least partially removed. Moreover, the cover 428 may be made from a disposable material, such as cotton, paper, etc., or from a more durable and washable material. In either event, the cover 428 may be removable, washable, and/or replaceable to ensure continued hygienic use of the cosmetic applicator 420, in contrast to classic sponges, brushes and blender make-up applicators that cannot be washed or partially replaced. The cover 428 may also be treated with an antibacterial solution to ensure hygiene with usage.

It can be appreciated from the foregoing that a removable, replaceable, and/or disposable cover 428 allows for the cosmetic applicator 420 to be used for various different needs and effects, such as different make-up looks (e.g., from matte to glow, from subtle to full coverage, etc.) and different functions (e.g., make-up application, make-up or nail polish removal, skin cleansing, hair/scalp applicator, etc.). For make-up use, the user will be able to use one body customized with different covers to apply different cosmetic formulations for different make-up results.

Figure 10:
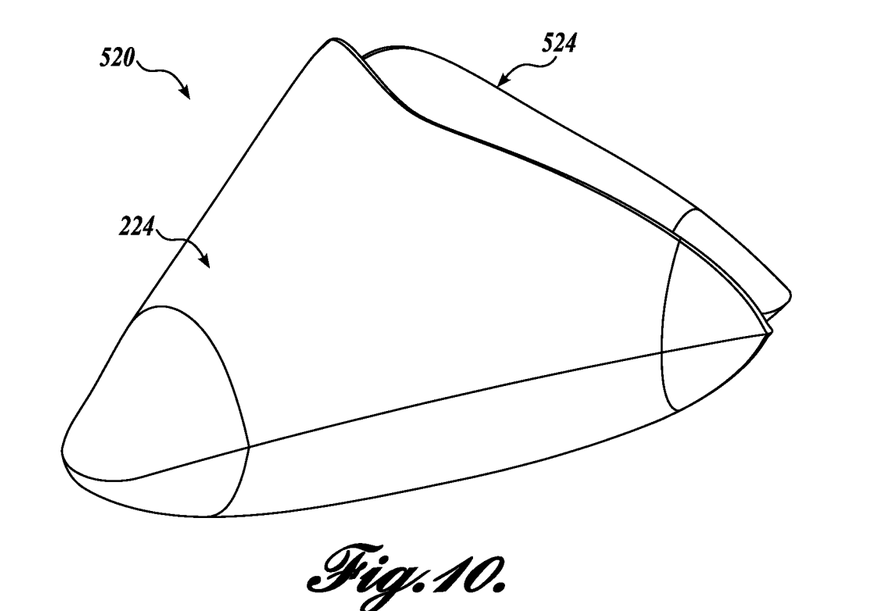
FIG. 10 is an isometric view of a cosmetic applicator formed in accordance with another alternative exemplary embodiment of the present disclosure.
Figure 11:
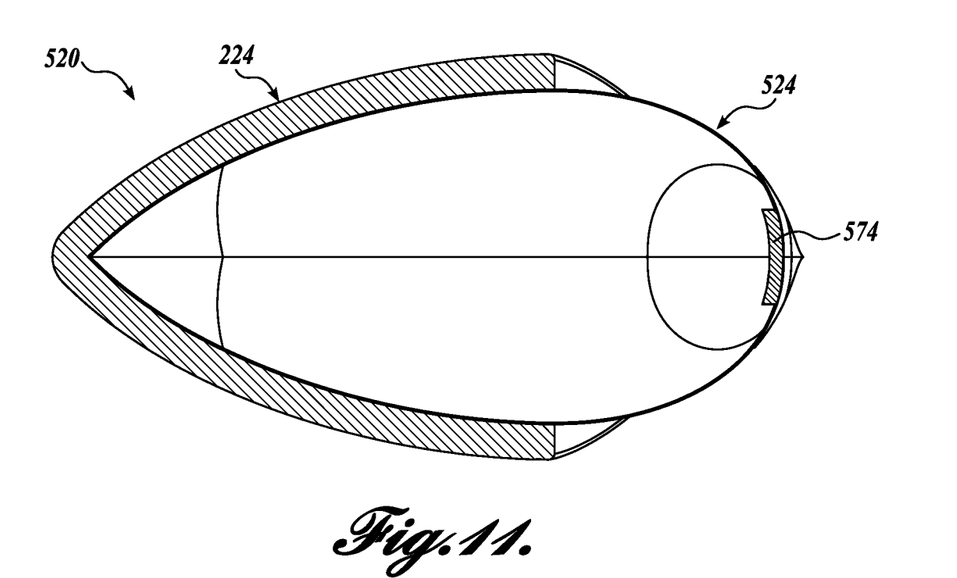
FIG. 11 is a cross-sectional view of the cosmetic applicator of FIG. 10.
Figure 12:
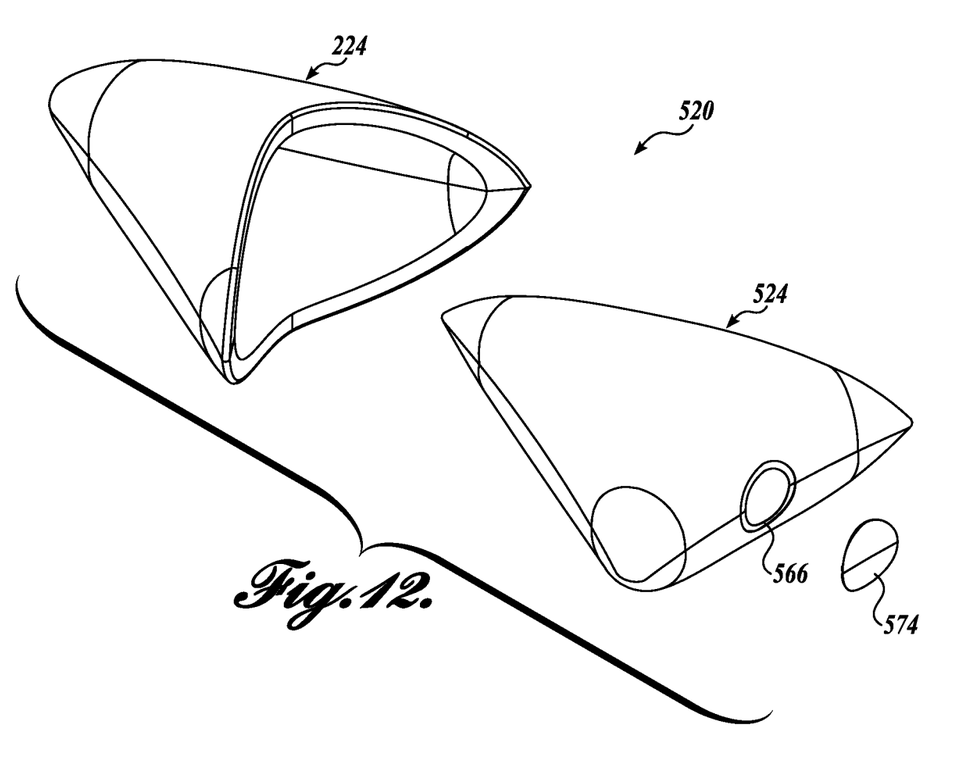
FIG. 12 is an exploded view of the cosmetic applicator of FIG. 10.

Referring to FIGS. 10-12, another alternative exemplary embodiment of a cosmetic applicator 520 is depicted where a second hollow body 524 is (optionally removably) received within the hollow interior of the hollow body 224 (described above with respect to FIG. 6). The hollow body 524 is substantially identical to the hollow body 324 described above with reference to FIG. 7 except that it has a thinner body wall. In that regard, the significantly thicker hollow body 524 received thereon increases at least a portion of the rigidity of the cosmetic applicator 520.

As can be appreciated, any suitable hollow body may be stacked on or otherwise disposed on another hollow body to increase rigidity of the cosmetic applicator, provide a different textured surface, etc. Along the same lines, any suitable hollow body may be stacked on or otherwise disposed on a pressurized core, such as those illustrated and described in U.S. patent application Ser. No. 15/693,312, filed Aug. 31, 2017, entitled "Cosmetic Applicator", the entire disclosure of which is hereby incorporated by reference herein. The stacked hollow bodies or stacked hollow bodies and cores may optionally be covered by a removable cover, such as cover 428 described above.

Figure 15:
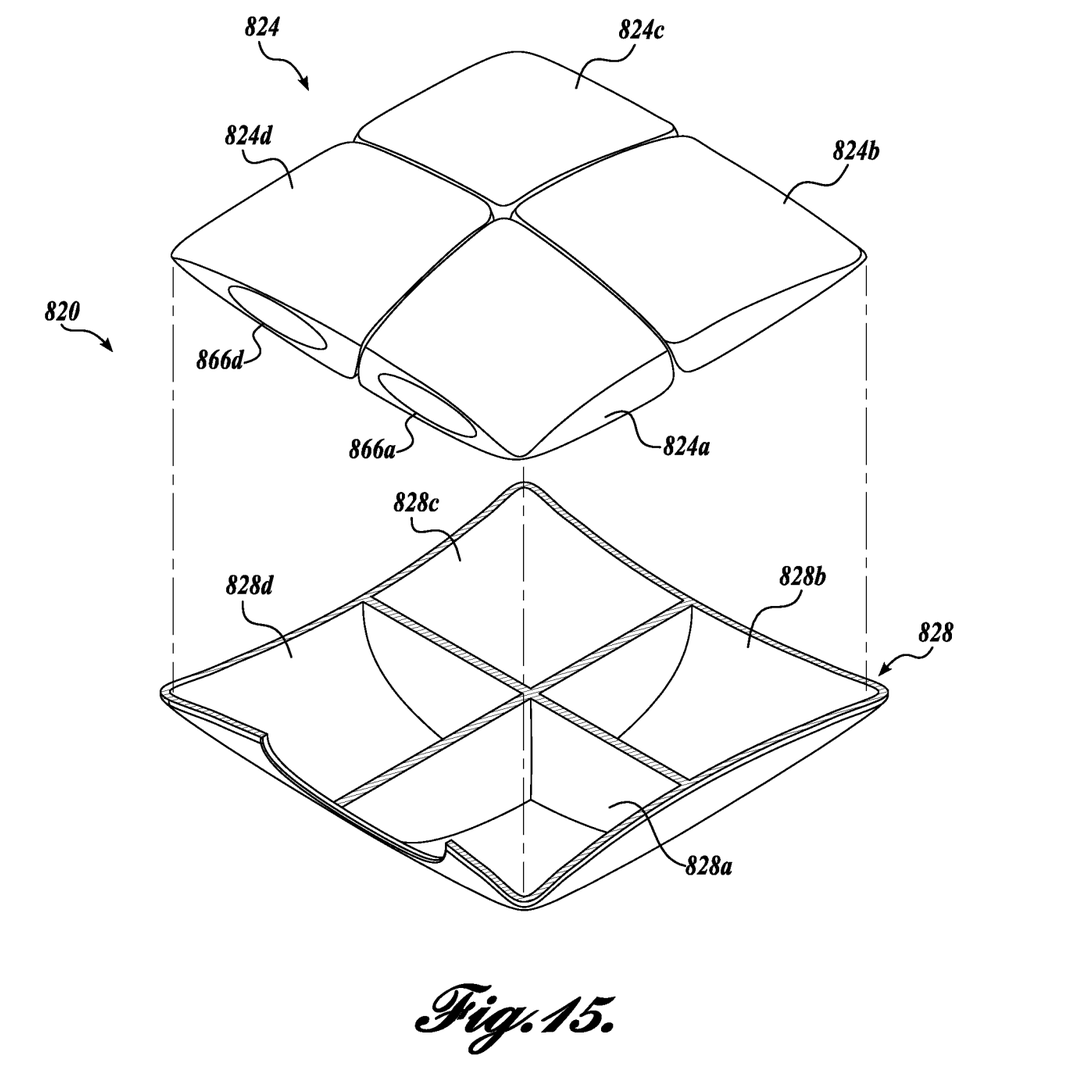
FIG. 15 is an isometric view of a cosmetic applicator formed in accordance with another alternative exemplary embodiment of the present disclosure.

Referring to FIG. 15, a cosmetic applicator 820 formed in accordance with another alternative exemplary embodiment of the present disclosure is depicted. The cosmetic applicator 820 includes multiple hollow, unpressurized bodies 824a, 824b, 824c, and 824d that are receivable within a cover 828 having a corresponding number of sleeves or pockets 828a, 828b, 828c, and 828d. In the depicted embodiment, the hollow, unpressurized bodies 824a, 824b, 824c, and 824d and corresponding pockets 828a, 828b, 828c, and 828d are generally square shaped, and the overall shape of the cosmetic applicator 820 is generally square shaped. However, it should be appreciated that the cosmetic applicator 820 may instead be triangle-shaped or any other suitable shape.

Each pocket 828a, 828b, 828c, and 828d may have an opening (only openings 866a and 866d shown) such that the bodies 824a, 824b, 824c, and 824d may be removably receivable therein. It can be appreciated that each body 824a, 824b, 824c, and 824d may be uniquely chosen (i.e., material, thickness, overall rigidity, surface pattern, etc.) to create a cosmetic applicator 820 having different areas of firmness, rigidity, resiliency, malleability, sensorial effects, etc. In the alternative or in addition thereto, each pocket 828a, 828b, 828c, and 828d may be made from a unique material, and/or have a unique coating, and/or have a unique surface configuration, pattern, texture, etc., to create a single cosmetic applicator 820 having various applications or uses. For instance, a softer hollow body may be received within a more textured pocket to provide suitable abrasion of a surface, whereas a firmer hollow body may be received within a less textured or smoother pocket for a non-abrasive application. It should be appreciated that any suitable combination of features or configurations may be used.

With the above-described features in mind, the cosmetic applicators shown and described herein can be configured to deposit/transfer a cosmetic formulation onto the surface of the skin and leave a continuous film that merges/fits beautifully with the skin for a second-skin effect while providing desired sensorial effects to the user. Moreover, the cosmetic applicators can be configured to remove a cosmetic formulation film, and substantially only the film, without damaging the skin surface or any sensitive areas. With the user having a choice of the body and/or the cover and/or an interior component (core, plug, webbing, etc.), the cosmetic applicator can produce individual and satisfying sensorial and aesthetic results for the user.

The detailed description set forth above in connection with the appended drawings is intended as a description of exemplary embodiments of the disclosed subject matter and is not intended to represent the only embodiments. The exemplary embodiments described in this disclosure are provided merely as examples or illustrations of a cosmetic applicator and should not be construed as preferred or advantageous over other embodiments. The illustrative examples provided herein are not intended to be exhaustive or to limit the disclosure to the precise forms disclosed. Similarly, any features and/or process steps described herein may be interchangeable with other features and/or process steps, or combinations of features and/or process steps, in order to achieve the same or substantially similar result.

In the foregoing description, numerous specific details are set forth in order to provide a thorough understanding of the exemplary embodiment of the present disclosure. It will be apparent to one skilled in the art, however, that many embodiments of the present disclosure may be practiced without some or all of the specific details. In some instances, well-known features, subassemblies, and/or process steps have not been described in detail in order not to unnecessarily obscure various aspects of the present disclosure. Further, it will be appreciated that embodiments of the present disclosure may employ any combination of features described herein. For instance, any feature or configuration described above with respect to the core may be adapted for use with the cover, and vice versa.

Although certain descriptive terms are used to illustrate or describe certain aspects or benefits of the present invention, they should not be seen as limiting. For instance, although the term "applicator" is used, it should be appreciated that any or all of the cosmetic applicators described and illustration herein may also be used for cleansing, removal of cosmetic formulation, treatment of skin conditions, or other uses.

The present disclosure also includes references to directions, such as "upper," "lower," "upward," "downward," "top," "bottom," "first," "second," etc. These references and other similar references in the present disclosure are only to assist in helping describe and understand the exemplary embodiments and are not intended to limit the claimed subject matter to these directions. The term "cosmetic formulation" or "cosmetic" (as used with the phrase "cosmetic applicator") should be interpreted broadly to include any cosmetic formulation, beauty product, lotion, lacquer, etc., generally applied to a person's skin, eyes, nails, or other body part. Moreover, it should be appreciated that the cosmetic applicator may also be adapted for other uses.

The present disclosure may also reference quantities and numbers. Unless specifically stated, such quantities and numbers are not to be considered restrictive, but exemplary of the possible quantities or numbers associated with the present disclosure. Also in this regard, the present disclosure may use the term "plurality" to reference a quantity or number. In this regard, the term "plurality" is meant to be any number that is more than one, for example, two, three, four, five, etc. The terms "substantially," "about," "approximately," etc., mean plus or minus 5% of the stated value.

While illustrative embodiments have been illustrated and described, it will be appreciated that various changes can be made therein without departing from the spirit and scope of the invention.

The invention claimed is:

1. A cosmetic applicator comprising a first body having a predetermined rigidity and made at least in part from a material that is resilient, the first body having at least first and second opposing sides, at least first and second soft edges defined between the first and second opposing sides and a hollow, unpressurized interior between the first and second opposing sides to define an overall pillow shaped first body, wherein each of the first and second opposing sides are generally convex in shape and taper toward at least one corner to define an area of increased rigidity of the first body, wherein the hollow, unpressurized interior of the first body is configured to receive an interior component for manipulating the applicator, and wherein the first body includes an opening providing access to the hollow, unpressurized interior.

2. The cosmetic applicator of claim 1, further comprising a plug removably receivable within the opening.

3. The cosmetic applicator of claim 2, wherein the size of the opening corresponds to at least one of the material of the first body and a wall thickness of the first body for at least partially determining a rigidity of the at least a portion of the first body.

4. The cosmetic applicator of claim 1, wherein the configuration of the plug corresponds to at least one of the material of the first body and a wall thickness of the first body for at least partially determining a rigidity of the at least a portion of the first body.

5. A cosmetic applicator comprising a first body having a predetermined rigidity and made at least in part from a material that is resilient, the first body having at least first and second opposing sides, at least first and second soft edges defined between the first and second opposing sides and a hollow, unpressurized interior between the first and second opposing sides to define an overall pillow shaped first body, wherein each of the first and second opposing sides are generally convex in shape and taper toward at least one corner to define an area of increased rigidity of the first body, wherein the hollow, unpressurized interior of the first body is configured to receive an interior component for manipulating the applicator, wherein the cosmetic applicator further comprises a coating or film, and wherein the cosmetic applicator includes at least a first area coated with a first material and second area coated with a second material different from the first material.

6. The cosmetic applicator of claim 5, wherein the hydrophilic material is chosen from a group consisting of polyvinylpyrolidone (PVP), polyurethanes, polyacrylic acid (PAA), polyethylene oxide (PEO), polysaccharides, and any combination thereof.

7. The cosmetic applicator of claim 5, wherein the hydrophobic material is chosen from a group consisting of manganese oxide polystyrene (MnO2/PS) nano-composite, zinc oxide polystyrene (ZnO/PS) nano-composite, precipitated calcium carbonate[3], carbon nano-tube structures, silica nano-coating, and any combination thereof.

8. A cosmetic applicator comprising a first body having a predetermined rigidity and made at least in part from a material that is resilient, the first body having at least first and second opposing sides, at least first and second soft edges defined between the first and second opposing sides and a hollow, unpressurized interior between the first and second opposing sides to define an overall pillow shaped first body, wherein each of the first and second opposing sides are generally convex in shape and taper toward at least one corner to define an area of increased rigidity of the first body, wherein the hollow, unpressurized interior of the first body is configured to receive an interior component for manipulating the applicator, wherein the cosmetic applicator further comprises a coating or film, and wherein a first portion of the cosmetic applicator includes a hydrophilic material and a second portion includes a hydrophobic material.

9. A cosmetic applicator comprising a first body having a predetermined rigidity and made at least in part from a material that is resilient, the first body having at least first and second opposing sides, at least first and second soft edges defined between the first and second opposing sides and a hollow, unpressurized interior between the first and second opposing sides to define an overall pillow shaped first body, wherein each of the first and second opposing sides are generally convex in shape and taper toward at least one corner to define an area of increased rigidity of the first body, wherein the hollow, unpressurized interior of the first body is configured to receive an interior component for manipulating the applicator, and wherein at least one of a portion of the first body is treated with a plasma treatment.

10. A cosmetic applicator comprising a first body having a predetermined rigidity and made at least in part from a material that is resilient, the first body having at least first and second opposing sides, at least first and second soft edges defined between the first and second opposing sides and a hollow, unpressurized interior between the first and second opposing sides to define an overall pillow shaped first body, wherein each of the first and second opposing sides are generally convex in shape and taper toward at least one corner to define an area of increased rigidity of the first body, wherein the hollow, unpressurized interior of the first body is configured to receive an interior component for manipulating the applicator, and wherein the cosmetic applicator further comprises a second body having a hollow, unpressurized interior removably securable on the first body.

11. A cosmetic applicator comprising:
a first body having a predetermined rigidity and made at least in part from a material that is resilient, the first body having at least first and second opposing sides, at least first and second soft edges defined between the first and second opposing sides, and a hollow, unpressurized interior between the first and second opposing sides, wherein each of the first and second opposing sides are generally convex in shape and taper toward at least one corner to define an area of increased rigidity of the first body, and wherein the hollow, unpressurized interior of the first body is configured to receive an interior component for manipulating the applicator; and
a cover removably securable on the first body.

12. A cosmetic applicator comprising a first body having a predetermined rigidity and made at least in part from a material that is resilient, the first body having at least first and second opposing sides, at least first and second soft edges defined between the first and second opposing sides and a hollow, unpressurized interior between the first and second opposing sides to define an overall pillow shaped first body, wherein each of the first and second opposing sides are generally convex in shape and taper toward at least one corner to define an area of increased rigidity of the first body, wherein the hollow, unpressurized interior of the first body is configured to receive an interior component for manipulating the applicator, and wherein the hollow, unpressurized interior of the first body is configured to receive at least one of a user's finger, a plug, a pressurized core, and a cosmetic tool.

* * * * *